United States Patent [19]

Gray

[11] Patent Number: 5,040,542
[45] Date of Patent: Aug. 20, 1991

[54] BONE BIOPSY NEEDLE

[76] Inventor: Norman Gray, 111 Woodwinds Industrial Ct., Cary, N.C. 27511

[21] Appl. No.: 489,386

[22] Filed: Mar. 5, 1990

[51] Int. Cl.⁵ ............................................. A61B 10/00
[52] U.S. Cl. ..................................... 128/754; 606/179
[58] Field of Search ....................... 128/751, 753, 754; 606/179, 184, 167, 180

[56] References Cited

U.S. PATENT DOCUMENTS

| | | | |
|---|---|---|---|
| 1,167,014 | 1/1916 | O'Brien | 128/751 |
| 2,505,358 | 4/1949 | Gusberg et al. | 128/751 |
| 4,798,213 | 1/1989 | Doppelt | 128/754 |

Primary Examiner—William E. Kamm
Assistant Examiner—Kennedy J. Schaetzle
Attorney, Agent, or Firm—John C. Smith, Jr.

[57] ABSTRACT

A bone biopsy instrument kit includes a hollow needle with an annular cutting edge which is rotated to cut a core of bone sample which is retained in the internal passage of the needle. A semi-circular portion of the needle wall is removable to withdraw the core sample without compressing or otherwise changing the consistency of the sample. The annular cutting edge has a sawtooth configuration with a side rake angle causing bone dust to be expelled radially without contaminating the core sample. An elongated obturator and an elongated trocar may be inserted through the needle to direct the annular cutting edge through tissue and to center and guide the instrument into the surface of the bone.

15 Claims, 2 Drawing Sheets

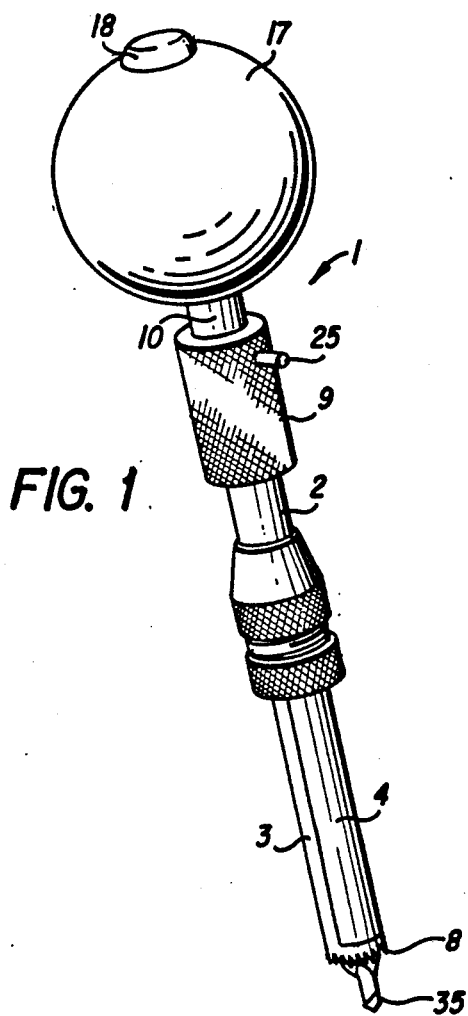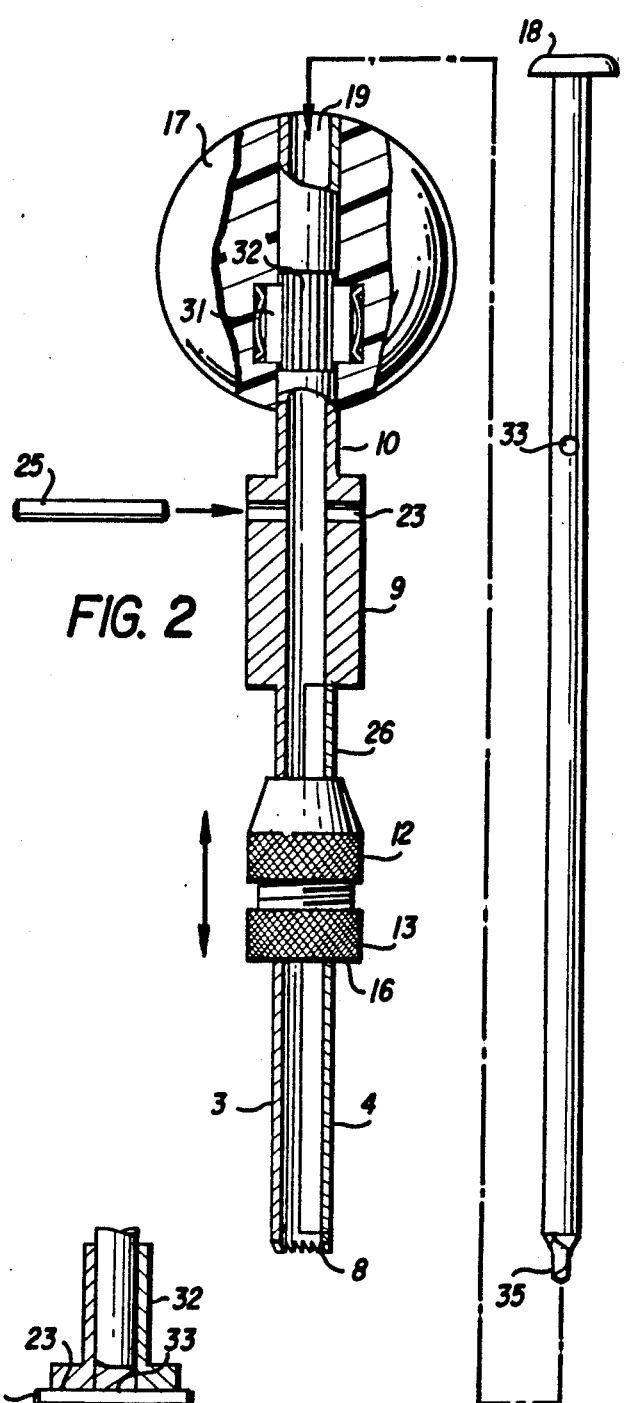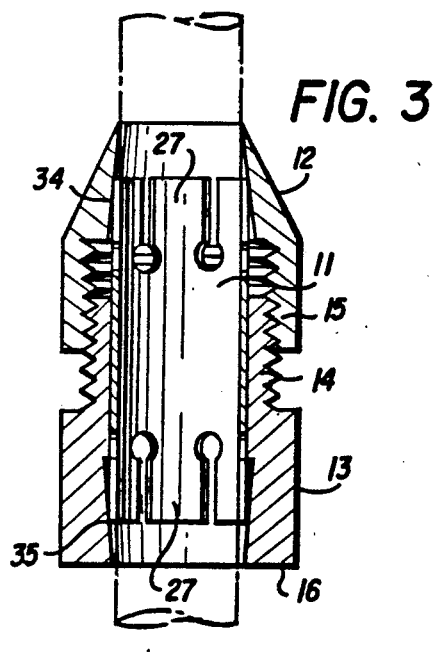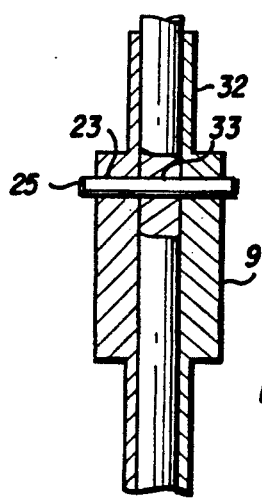

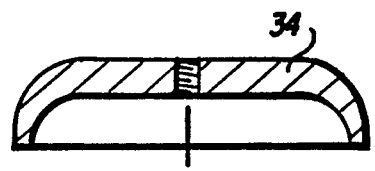
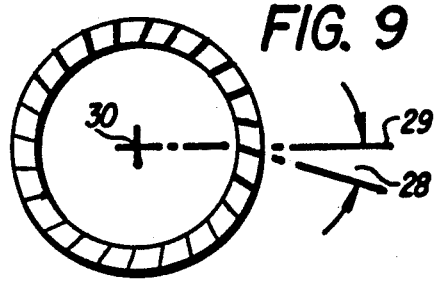
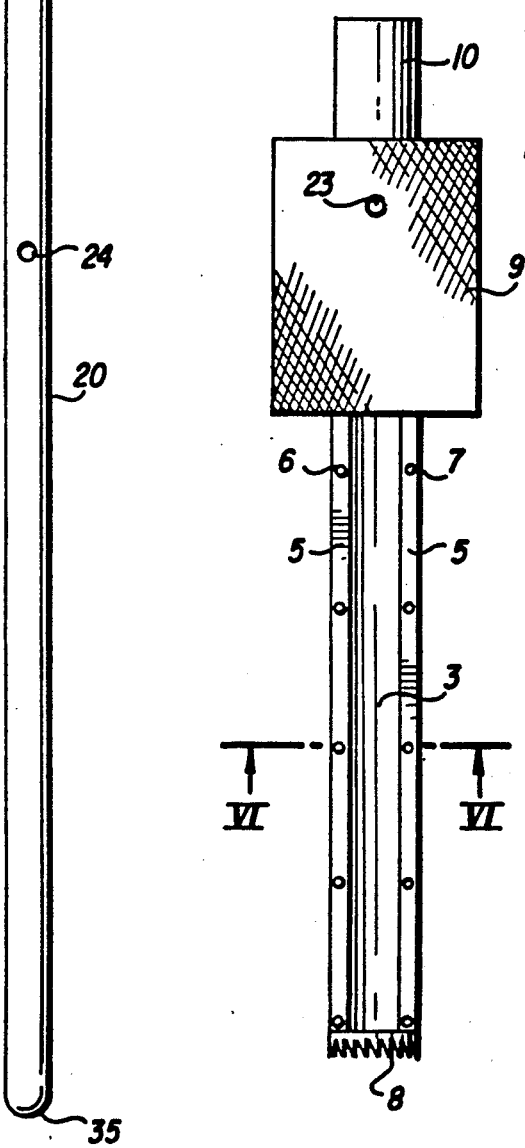
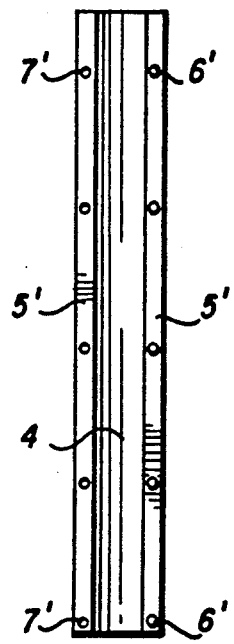
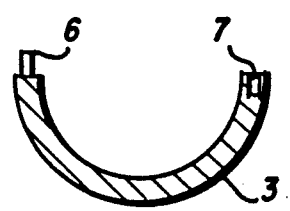

BONE BIOPSY NEEDLE

BACKGROUND OF THE INVENTION

The present invention relates to an improved bone biopsy instrument for use by the medical profession for obtaining biopsy samples of bone from a human patient.

Bone biopsy instruments, and particularly bone biopsy needles, are well known in the prior art. However, these prior art needles have been cumbersome and tedious in use and not always effective for their intended purpose. Among the disadvantages are contamination of the sample collected in the interior passage of the needle as the needle is driven through the bone, destruction of the consistency of the sample during removal of the sample from the interior passage of the needle by use of force, the inability to accurately gauge the depth to which the cutting edge of the needle is driven by the user into the bone, the need for an excessive number of components by the user resulting in a prolonged procedure, etc.

Prior art bone biopsy instruments are illustrated and described, for example, in the following U.S. patents:

| | |
|---|---|
| 3,175,554 | Stewart |
| 3,913,566 | Lacey |
| 4,010,737 | Vilaghy et al. |

An object of the present invention is a bone biopsy instrument which has a very limited number of components and consequently simplifies the extraction of a bone sample.

A further object of the invention is a bone biopsy instrument capable of cutting bone without contaminating the sample.

A still further object of the invention is a bone biopsy instrument capable of providing a sample without destroying the consistency and integrity of the sample.

A still further object of the invention is a bone biopsy instrument having an adjustable gauge for visually and accurately determining the location of the cutting edge of the instrument as it is cutting into the bone.

These and other objects and advantages of the present invention will become apparent from the following detailed description when read in conjunction with the drawings.

BRIEF DESCRIPTION OF THE DRAWINGS

FIG. 1 is a perspective view of the bone biopsy instrument of the present invention;

FIG. 2 is a side view, partially in cross-section, of the bone biopsy instrument of FIG. 1 with the trocar removed from the needle;

FIG. 3 is a detailed view, partially in cross-section, of the means for securing together the two semi-cylindrical sections forming the hollow needle shown in FIG. 2;

FIG. 4 is a view, partially in cross-section, showing the means for releasably securing the trocar in place in the hollow needle shown in FIG. 2;

FIG. 5 is a side view of one of the semi-cylindrical sections of the hollow needle shown in FIG. 2;

FIG. 6 is a cross-sectional view of the one semi-cylindrical section of the hollow needle taken along the line VI—VI of FIG. 5;

FIG. 7 is a side view of the other of the semi-cylindrical sections of the hollow needle shown in FIG. 2;

FIG. 8 is a side view of an obturator for use with the hollow needle shown in FIG. 2; and FIG. 9 is an end view of the cutting edge of the bone biopsy instrument of FIG. 1.

DETAILED DESCRIPTION OF THE PREFERRED EMBODIMENT

Referring to the drawings, the bone biopsy instrument 1 of the present invention comprises an elongated, hollow, cylindrical needle 2 composed of two semi-cylindrical sections 3, 4 which together form a passage 26 extending the full length of the needle. The primary semi-cylindrical section 3 is illustrated in detail in FIGS. 5 and 6, and the secondary semi-cylindrical section 4 is illustrated in FIG. 7. The longitudinal surfaces 5 of the semi-cylindrical section 3 abut the longitudinal surfaces 5' of the semi-cylindrical section 4 when the hollow needle is assembled. One of these two surfaces 5, 5' of each section has a plurality of spaced pins 6, 6' projecting therefrom, and the other of the elongated surfaces of the same section contains a plurality of spaced recesses 7, 7' which register with the pins of the other semi-cylindrical section when the two sections are assembled. This assures that proper alignment of the two semi-cylindrical sections 3, 4 when assembled will be maintained.

The lower end of the hollow needle 2 has an annular cutting ring 8 composed of a plurality of sawteeth for cutting out a cylindrically shaped bone sample during rotation of the needle. The cutting ring 8 is secured to the semi-cylindrical section 3 and abuts the adjacent end of the other semi-cylindrical section 4. The cutting ring 8 has a buttress-type cutting edge which displaces bone dust radially outwardly during rotary cutting of the bone to avoid contamination of the core sample. As shown in FIG. 9, the teeth are at about a 15° side rake 28 with respect to a line 29 passing through the axis 30 of the cutting ring 8 to displace the bone dust radially outwardly.

Spaced from the annular cutting ring 8 of the needle 2 is an enlarged portion 9 which may be an integral part of the semi-cylindrical section 3. The enlarged portion 9 serves to increase stability of the cutting edge 8 during cutting of the bone. The adjacent end of the semi-cylindrical section 4 abuts the enlarged portion. The exterior surface of the end 10 of the needle 2 opposite the annular cutting edge 8 has a square configuration 28 for reasons which will become apparent later.

Surrounding the needle 2 is an annular spring sleeve 11 which is slidable along the outer surface of the needle. The sleeve has a plurality of extensions 27 along opposite sides. Surrounding the annular spring sleeve 11 are a pair of annular members 12, 13 for tightening the sleeve 11 against the outer surface of the needle 2. The inner surfaces of both annular members 12 and 13 each have a conical configuration 34, 35 which extends beyond the respective extensions 27 of the annular sleeve 11 and presses against the extensions. Annular member 13 includes a male-threaded portion 14 and annular member 12 has a corresponding female-threaded portion 15. The exterior surfaces of both annular members 12 and 13 are knurled such that they can be manually gripped and rotated relative to each other to move the annular members 12, 13 closer together and thereby, by means of the conical inner surfaces 34, 35, compress the extensions 27 of the annular spring sleeve 11 tightly against the exterior surface of the needle 2, holding the semi-cylindrical sections 3, 4 together. Relative rotation of the annular members 12, 13 in the opposite directions moves the annular members apart, releasing pressure on the extensions 27 and permitting the sleeve 11 and annular members 12, 13 to move along the length of the needle 2.

The sleeve 11 and annular members 12, 13 serve not only to firmly secure together the two semi-cylindrical sections 3, 4 but also to act as a guide or depth gauge during use of the bone biopsy instrument. The position of the sleeve and annular members along the needle 2 may be adjusted such that the end surface 16 of annular member 13 is set at a predetermined distance from the annular cutting edge of the cutting ring 8 for reasons which will become apparent later.

A handle 17 is releasably positioned over the end 10 of the needle 2, the handle having a passage 19 in alignment with the passage 26 in the needle. Optionally, the handle 17 may contain a one-way ratchet mechanism 31 for rotating the needle 2 during cutting of the bone by the cutting edge 8. The ratchet mechanism includes a square sleeve 32 in the passage 19 for receiving the square end 10 of the needle 2. The ratchet mechanism permits rotation of the handle and needle in one direction, e.g. clockwise as viewed from the top of the handle, and free rotation of the handle in the opposite direction while the needle remains stationary. Such one-way ratchet mechanisms are well known in the art as, for example, is disclosed in detail in U.S. Pat. No. 2,656,865 to Bright which is incorporated by reference in its entirety. Utilization of the ratchet mechanism in the handle assures that the needle will be rotated in only one direction, thereby minimizing the possibility that the needle 2 will be rotated in the opposite direction, causing bone dust generated by the cutting edge to be propelled inwardly by the teeth of the cutting edge of the cutting ring 8 and contaminate the core sample.

Alternatively, the end 10 of the needle 2 may be round with at least one projecting key for engaging a corresponding keyhole in the sleeve 32 of the ratchet mechanism 31 to releasably secure the handle 17 on the end of the needle 2.

Before using the bone biopsy instrument, the distance between the surface of the skin at the point of entry of the needle and the surface of the bone at the side opposite the point of entry is determined. Then the position of the end 16 of the annular member 13 is adjusted to a predetermined distance from the cutting edge of the cutting ring 8 as described above. This distance is slightly less than the measured distance between the surface of the skin at the point of entry of the needle and the surface of the bone on the side opposite the point of entry.

When using the bone biopsy instrument, an obturator 20 (see FIG. 8) having a rounded end 31 and a head 34 secured on to the opposite end is first inserted through the passage 19 in the handle 17 and the passage 26 of the needle 2 and is locked in position with a removable pin 25 passing through bore 23 in the enlarged portion 9 and bore 24 in the obturator 20. When locked in position, the smooth rounded end 31 of the obturator 20 projects a short distance beyond the annular cutting edge of the cutting ring 8. When the bone biopsy instrument is first used, the rounded end 31 of the obturator 20 serves as a guide as the bone biopsy instrument is pressed through the soft tissue and muscle towards the surface of the bone of the patient. The rounded end 31 serves to guide the adjacent cutting edge of the cutting ring 8 towards the surface of the bone with minimal damage to the soft tissue and muscle.

Upon the rounded end 31 of the obturator 20 contacting the surface of the bone, the obturator 20 is withdrawn by gripping the head 34, after removing the pin 25, through the needle 2 and handle 17 while the bone biopsy instrument is held in place, and in place thereof a trocar 32, having a head 18, is inserted through the handle 17 and needle 2, the trocar being locked in position by the pin 25 passing through bore 23 in the enlarged portion 9 and the bore 33 in the trocar 32. The lead end of the trocar 32 has a carbide cutting tip 35 with a pointed end which serves to center and guide the bone biopsy instrument into the surface of the bone as the bone biopsy instrument is rotated. When the cutting edge of the cutting ring 8 has reached the surface of the bone and cutting of the bone has begun such that the needle 2 is firmly in place relative to the bone, the trocar 32 is withdrawn, after withdrawing the locking pin 25, after which cutting into the bone is continued. As the needle 8 is rotated and the cutting ring 8 cuts more deeply into the bone, the cylindrical bone sample is fed upwardly into the passage 26 of the needle 2.

The position of the end 16 of the annular member 13, having been adjusted before using the bone biopsy instrument, the operator of the instrument can observe, by the distance of the end 16 of annular member 13 from the surface of the skin of the patient, when the cutting edge is about to reach the surface of the bone on the side opposite the point of entry. At this point the operator can more slowly and carefully rotate the bone biopsy instrument during the final cutting stage to avoid unnecessary splintering of the opposite surface of the bone as it is pierced by the cutting edge (thus avoiding contamination of the core sample in the passage 26 of the needle 2.)

The needle 2 is then withdrawn from the bone with the core sample contained in the passage 26. To remove the core sample, the annular members 12, 13 are loosened, and the annular members with the annular spring sleeve 11 are removed by sliding them along the needle and over the cutting ring 8. The semi-cylindrical section 4 is then removed, exposing the core sample which is then removed laterally from the passage 26. Removal of the core sample is accomplished without destroying the integrity of the core sample. No ramming of the core sample to push the sample axially along the passage of the needle is necessary to remove the sample from the needle.

The bone biopsy instrument of the present invention offers substantial advantages over the prior art. The combination of the annular spring sleeve 11 with the annular members 12 and 13 provides an accurate adjustable depth gauge to insure that the user is fully aware of the location of the cutting edge of the cutting ring 8 in the bone. The combination of the ratchet mechanism associated with the handle and the side rake of the teeth of the cutting ring 8 insures that the bone dust generated during the cutting operation will be directed away from the core sample as it is introduced into the passage 26 of the needle 2. Removal of the sample from the passage of the needle is accomplished without destroying the integrity of the sample due to the fact that the sample is readily accessible and can be removed without applying pressure to the sample.

Although preferred embodiments of the invention have been disclosed for purposes of illustration, it will be evident that various changes and modifications may be made therein which fall within the scope of the present invention.

I claim:

1. A bone biopsy instrument kit comprising:
   (a) an elongated hollow cylindrical needle having a passage therethrough and an annular cutting edge at one end thereof, said needle comprising a first elongated section, at least a portion of its length having a semi-cylindrical configuration as viewed in cross-section, and a second elongated section having a semi-cylindrical configuration as viewed in cross-section, each said section having a pair of surfaces which abut the respective surfaces of the other section to form said hollow needle;
   (b) means for releasably securing said semi-cylindrical sections together with said pairs of surfaces in abutting relationship;
   (c) a handle having means releasably engaging the end of said needle opposite said one end, said handle having a straight passage therethrough in alignment with said passage in said needle;
   (d) an elongated trocar having a point at one end and extending through said passages in said handle and needle and positioned with said point projecting beyond said annular cutting edge; and
   (e) means for releasably securing said trocar in said position in said needle;
   (f) whereby said hollow needle with said point of said trocar extending beyond said annular cutting edge may be rotated to cut into the surface of a bone, said trocar withdrawn through said handle, said annular cutting edge of said needle driven a predetermined distance through said bone with a sample of said bone retained in said passage in said needle, said needle withdrawn from said bone with said sample retained in said passage, and said first and second sections of said needle separated to remove said sample.

2. A bone biopsy instrument kit according to claim 1 wherein said annular cutting edge at said one end of said needle has a sawtooth configuration.

3. A bone biopsy instrument kit according to claim 2 wherein said elongated hollow cylindrical needle further comprises an annular cutting ring having said sawtooth configuration, said annular cutting ring being secured to said first elongated section at said one end of said needle.

4. A bone biopsy instrument kit according to claim 3 wherein said sawtooth configuration of said cutting ring comprises a plurality of sawteeth arranged sequentially about said cutting edge, said teeth being at a side rake angle with respect to a line passing through the axis of said cutting ring such that bone dust generated during cutting is displaced radially outwardly as said needle is rotated in one direction.

5. A bone biopsy instrument kit according to claim 4 wherein said side rake angle is about 15°.

6. A bone biopsy instrument kit according to claim 1 wherein at least one of said pair of surfaces on one of said sections has at least one projection and at least one of said pair of surfaces on the other of said semi-cylindrical sections has at least one corresponding recess which at least one projection and at least one recess register when said sections are assembled to form said needle to maintain alignment of said semi-cylindrical sections.

7. A bone biopsy instrument kit according to claim 1 wherein said means for releasably securing said sections together comprises at least one annular member surrounding a portion of the length of said needle.

8. A bone biopsy instrument kit according to claim 7 wherein said at least one annular member is slidable along a substantial length of said needle and includes means for securing said annular member at any predetermined position along said length whereby said at least one annular member serves as an indicator of the depth of said cutting edge in said bone.

9. A bone biopsy instrument kit according to claim 7 wherein said at least one annular member comprises a first annular member surrounding a portion of the length of said needle and means for pressing at least a portion of said first annular member tightly against the surface of said needle to prevent said first annular member from moving axially along the length of said needle.

10. A bone biopsy instrument kit according to claim 9 wherein said means for pressing said first annular member against the surface of said needle comprises second and third annular members having corresponding male and female-threaded members respectively surrounding said needle and said first annular member, the interior surfaces of said second and third annular members being conical shaped such that when said second and third annular members are screwed towards each other said first annular member is cammed into tight engagement with the surface of said needle.

11. A bone biopsy instrument kit according to claim 1 wherein at least one of said sections of said needle comprises an enlarged portion spaced from said annular cutting edge for reinforcing said needle and increasing stability of said cutting edge.

12. A bone biopsy kit instrument according to claim 1 wherein the geometrical configuration of the portion of said hollow needle adjacent said opposite end is non-cylindrical and said means at one end of said handle for releasably engaging said opposite end of said needle comprises a recess having a corresponding geometrical configuration therein whereby said hollow needle may be rotated during cutting of said bone by rotating said handle.

13. A bone biopsy instrument kit according to claim 12 wherein said handle further comprises ratchet means permitting said needle to be rotated by rotation of said handle in only one direction, said needle being stationary during rotation of said handle in the opposite direction.

14. A bone biopsy instrument kit according to claim 1 further comprising an aperture passing through each of said sections of said needle and said trocar when said trocar is in said normal position with said point projecting beyond said annular cutting edge, and removable pin means positioned in said aperture to retain said trocar in position in said needle, whereby said trocar may be withdrawn from said passage in said needle after withdrawing said pin from said aperture.

15. A bone biopsy instrument kit according to claim 1 further comprising an elongated obturator rounded at one end and adapted to extend through said passages in said handle and needle, in place of said trocar, said releasable securing means securing said obturator in place with said rounded end projecting beyond said annular cutting edge to serve as a guide as said bone biopsy instrument is pressed through the soft tissue and muscle towards the surface of the bone of a patient.

* * * * *